United States Patent
Fung et al.

(10) Patent No.: US 10,813,793 B2
(45) Date of Patent: Oct. 27, 2020

(54) ARTICLE AND METHOD FOR NEGATIVE PRESSURE WOUND THERAPY

(71) Applicant: 3M INNOVATIVE PROPERTIES COMPANY, St. Paul, MN (US)

(72) Inventors: Simon S. Fung, Woodbury, MN (US); Chaodi Li, Woodbury, MN (US); Brittany A. Akehurst, Bloomington, MN (US); Jie Liu, Woodbury, MN (US); James M. Sieracki, Plymouth, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 632 days.

(21) Appl. No.: 15/129,434

(22) PCT Filed: Mar. 25, 2015

(86) PCT No.: PCT/US2015/022440
§ 371 (c)(1),
(2) Date: Sep. 27, 2016

(87) PCT Pub. No.: WO2015/148636
PCT Pub. Date: Oct. 1, 2015

(65) Prior Publication Data
US 2017/0172806 A1     Jun. 22, 2017

Related U.S. Application Data

(60) Provisional application No. 61/971,679, filed on Mar. 28, 2014.

(51) Int. Cl.
*A61F 13/00*     (2006.01)

(52) U.S. Cl.
CPC .. *A61F 13/00068* (2013.01); *A61F 13/00021* (2013.01); *A61F 13/00034* (2013.01); *A61F 2013/00327* (2013.01)

(58) Field of Classification Search
CPC .......... A61F 13/00068; A61F 13/00021; A61F 13/00034; A61F 2013/00327
(Continued)

(56) References Cited

U.S. PATENT DOCUMENTS

| 1,764,676 A | 6/1930 | Campbell |
| 4,112,947 A | 9/1978 | Nehring |

(Continued)

FOREIGN PATENT DOCUMENTS

| CN | 102002817 | 4/2011 |
| CN | 203246125 | 10/2013 |

(Continued)

OTHER PUBLICATIONS

China National Intellectual Property Administration, Search Report dated Nov. 21, 2018, for CN201580017124.3.
(Continued)

*Primary Examiner* — Andrew J Mensh
(74) *Attorney, Agent, or Firm* — 3M Innovative Properties Company; Trisha D. Adamson

(57) ABSTRACT

An article comprising a macroporous wound-packing material and a microcorrugated microporous wound-contact layer is provided. The wound packing material is coupled to and/or substantially surrounded by the wound-contact layer. The average pore diameter of the microporous layer is less than or equal to about 90 m. A method of treating a wound using a microcorrugated microporous wound-contact layer and a macroporous wound packing material is also provided.

21 Claims, 6 Drawing Sheets

(58) Field of Classification Search
USPC .......................................................... 604/319
See application file for complete search history.

(56) References Cited

U.S. PATENT DOCUMENTS

| | | | |
|---|---|---|---|
| 4,382,441 | A | 5/1983 | Svedman |
| 4,569,674 | A | 2/1986 | Phillips et al. |
| 4,655,754 | A | 4/1987 | Richmond et al. |
| 4,969,880 | A | 11/1990 | Zamierowski |
| 4,991,234 | A | 2/1991 | Greenberg |
| 5,298,015 | A * | 3/1994 | Komatsuzaki .... A61F 13/00021 424/444 |
| 5,358,494 | A | 10/1994 | Svedman |
| 5,636,643 | A | 6/1997 | Argenta et al. |
| 5,645,081 | A | 7/1997 | Argenta et al. |
| 6,060,079 | A * | 5/2000 | Freeman ................. A61K 9/703 424/447 |
| 6,071,304 | A | 6/2000 | Augustine et al. |
| 6,080,189 | A | 6/2000 | Augustine et al. |
| 6,095,992 | A | 8/2000 | Augustine |
| 6,270,792 | B1 | 8/2001 | Guillemet |
| 7,700,819 | B2 | 4/2010 | Ambrosio et al. |
| 2002/0161346 | A1 | 10/2002 | Lockwood |
| 2003/0120229 | A1 | 6/2003 | de Jong |
| 2005/0205840 | A1 | 9/2005 | Farneth et al. |
| 2007/0185426 | A1 * | 8/2007 | Ambrosio ................. A61L 27/52 602/43 |
| 2009/0234306 | A1 | 9/2009 | Vitaris |
| 2010/0063484 | A1 * | 3/2010 | Heagle .................... A61F 13/02 604/543 |
| 2010/0160874 | A1 * | 6/2010 | Robinson ............ A61M 1/0023 604/313 |
| 2010/0160877 | A1 * | 6/2010 | Kagan ................. A61M 1/0023 604/319 |
| 2010/0191196 | A1 | 7/2010 | Heagle |
| 2011/0257623 | A1 * | 10/2011 | Marshall ................. A61P 31/00 604/500 |
| 2011/0313383 | A1 | 12/2011 | Hofstetter |
| 2012/0116334 | A1 | 5/2012 | Albert et al. |
| 2013/0338613 | A1 | 12/2013 | Haggstrom et al. |
| 2014/0180229 | A1 * | 6/2014 | Fuller .................... A61L 15/22 604/360 |
| 2016/0270962 | A1 | 9/2016 | Wang |

FOREIGN PATENT DOCUMENTS

| | | |
|---|---|---|
| EP | 1 374 812 | 1/2004 |
| EP | 2 437 803 | 6/2013 |
| WO | WO 2003/045492 | 6/2003 |
| WO | WO 2008/005532 | 1/2008 |
| WO | WO 2013/007973 | 1/2013 |
| WO | WO 2013/175310 | 11/2013 |
| WO | WO 2014/062839 | 4/2014 |

OTHER PUBLICATIONS

Borgquist, O. et al.; "Tissue Ingrowth Into Foam but Not Into Gauze During Negative Pressure Wound Therapy"; Wounds; vol. 21, No. 11; 2009; pp. 302-309.

Chen, C.S. et al.; "Micropatterned Surface for Control of Cell Shape, Position, and Function"; Biotechnol. Prog.; vol. 14; 1998; pp. 356-363.

Ingber, D.E.; "Mechanical control of tissue growth: Function follows form"; PNAS; vol. 102, No. 33; 2005; pp. 11571-11572.

Jones, S.M. et al.; "Interface Dressings Influence the Delivery of Topical Negative-Pressure Therapy"; Plastic and Reconstructive Surgery; vol. 116, No. 4; 2005; pp. 1023-1028.

Kane, B.J. et al.; "Controlled induction of distributed microdeformation in wounded tissue via a microchamber array dressing"; Journal of Biomedical Materials Research A; vol. 95A, Issue 2; 2010; pp. 333-340.

Murphey, G.C. et al.; "Depth of penetration of negative pressure wound therapy into underlying tissues"; Wound Repair and Regeneration; vol. 17; 2009; pp. 113-117.

Pietramaggiori, G. et al.; "Tensile Forces Stimulate Vascular Remodeling and Epidermal Cell Proliferation in Living Skin"; Annals of Surgery; vol. 246, No. 5; 2007; pp. 896-902.

Saxena, V. et al.; "Vacuum-Assisted Closure: Microdeformations of Wounds and Cell Proliferation"; Plastic and Reconstructive Surgery; vol. 114, No. 5; 2004; pp. 1086-1096.

Wiegand, C. et al.; "Application of a drainage film reduces fibroblast ingrowth into large-pored polyurethane foam during negative-pressure wound therapy in an in vitro model"; Wound Repair and Regeneration; vol. 21; 2013; pp. 697-703.

Wilkes, R. et al.; "3D strain measurement in soft tissue: Demonstration of a novel inverse finite element model algorithm on MicroCT images of a tissue phantom exposed to negative pressure wound therapy"; Journal of the Mechanical Behavior of Biomedical Materials; vol. 2; 2009; pp. 272-287.

Wilkes, R. et al.; "Effects of Dressing Type on 3D Tissue Microdeformations During Negative Pressure Wound Therapy: A Computational Study"; Journal of Biomechanical Engineering; vol. 131; 2009; pp. 031012-1-031012-12.

China National Intellectual Property Administration Search Report for CN 201580017124.3, 3 pgs.

* cited by examiner

ARTICLE AND METHOD FOR NEGATIVE PRESSURE WOUND THERAPY

CROSS REFERENCE TO RELATED APPLICATIONS

This application is a national stage filing under 35 U.S.C. 371 of PCT/US2015/022440, filed Mar. 25, 2015, which claims priority to U.S. Provisional Patent Application No. 61/971,679, filed Mar. 28, 2014, the disclosure of which is incorporated by reference in its entirety herein.

BACKGROUND

Wound healing is a basic reparative process. It has been shown that dressing wounds with appropriate materials aids the natural regenerative process. Conventionally, such materials have been made from cotton fibers such as gauze. These dressings are beneficial to the healing process because they insulate damaged tissue from external contaminants and because they absorb potentially deleterious wound exudates. Devices and dressings that provide a moist wound environment for improved healing have been found to be useful.

Negative-pressure therapy has been used to facilitate removal of exudate from a wound area. When suction is applied to a gauze wound dressing, the dressing is compressed into a flattened state and any space between the gauze fibers is effectively eliminated. Additionally, even when wound exudates are being removed by suction from a gauze dressing, the gauze remains saturated and pressed against the wound, leaving no space above the wound and thus inhibiting new tissue growth.

When a foam dressing is used with suction, the pores of the foam collapse, eliminating space above the wound surface. Absent significant open space above the wound surface, new tissue grows into the foam when open-cell foam of certain porosity is used. Routine removal of the foam dressing causes disruption of new tissue as the tissue has grown into the foam pores, excessive bleeding, and unnecessary pain to the patient. In-growth of tissue into foam is a significant problem because the tissue has nowhere to grow but into the collapsed cell or pore structure of the foam. In contrast, dressings having an inflexible or rigid structured material placed in the wound cause unnecessary pain and discomfort in a patient and may not facilitate removal of liquid from the wound site.

A wound dressing for use in suction wound therapy preferably has some or all of the following characteristics and properties: the dressing should be flexible and conformable to the wound, the dressing should effectively enable transport of wound exudates away from the wound surface, and the dressing should allow sufficient voids above the wound when suction is applied for unobstructed new tissue growth. The dressing should maintain structural integrity when moist and should have a geometry that actively encourages tissue growth. The dressing should inhibit or minimize entanglement of healthy new tissue into the dressing material.

In spite of the advancements made in the dressings used for negative-pressure wound therapy, there remain issues that continually need to be addressed when using a wound dressing including ease of use, efficiency of tissue granulation, and the source of constant or varying negative pressure. Thus, there remains a need to constantly improve negative pressure wound dressings for open wounds.

SUMMARY

In general, the present disclosure is related to a method of wound therapy and an article for use in said method. In particular, the present disclosure relates to a method that places a microcorrugated microporous layer in contact with the wound surface, a macroporous wound-packing material adjacent the microporous layer, and a liquid-impermeable drape over said wound surface, microcorrugated microporous layer and wound-packing material. A source of negative pressure is placed into fluidic communication with the wound-packing material, thereby urging the wound surface against the microcorrugated microporous layer and drawing liquid (e.g., biological fluids) through the tissue and away from the wound surface. The inventive article of the present disclosure can be employed in the method to provide both the microcorrugated microporous layer and the macroporous wound-packing material arranged so that both can be applied to the wound surface simultaneously in the proper orientation.

In one aspect, the present disclosure provides an article. The article can comprise a macroporous wound-packing material coupled to a microcorrugated microporous wound-contact layer. The wound-contact layer comprises a plurality of micropores, the plurality having an average pore diameter. The average pore diameter of the micropores can be less than or equal to about 90 μm.

In another aspect, the present disclosure provides an article. The article can comprise a macroporous wound-packing material substantially enveloped in a microcorrugated microporous wound-contact layer. The wound-contact layer comprises a plurality of micropores, the plurality having an average pore diameter. The average pore diameter of the micropores can be less than or equal to about 90 μm.

In yet another aspect, the present disclosure provides a method. The method can comprise positioning a first major surface of a microcorrugated microporous layer in contact with a wound surface of a wound bed; positioning a macroporous wound-packing material proximate a second major surface of the microporous layer; covering the wound surface, the layer, and macroporous material with a liquid-impermeable drape; and placing the macroporous material into fluid communication with a source of negative pressure. The microporous layer can be dimensioned for positioning in the wound bed. The microporous layer can comprise a plurality of micropores, the plurality having an average pore diameter. The average pore diameter of the micropores can be less than or equal to about 90 μm. Positioning the macroporous material proximate the microporous layer can comprise positioning the microporous layer between the wound surface and the macroporous material.

In yet another aspect, the present disclosure provides a kit. The kit can comprise an article. The article can comprise a macroporous wound-packing material coupled to a microcorrugated microporous wound-contact layer. The wound-contact layer comprises a plurality of micropores, the plurality having an average pore diameter. The average pore diameter of the micropores can be less than or equal to about 90 μm.

In yet another aspect, the present disclosure provides a kit. The article can comprise a macroporous wound-packing material substantially enveloped in a microcorrugated microporous wound-contact layer. The wound-contact layer comprises a plurality of micropores, the plurality having an average pore diameter. The average pore diameter of the micropores can be less than or equal to about 90 μm.

In yet another aspect, the present disclosure provides a kit. The kit can comprise a microcorrugated microporous layer comprising a plurality of micropores and a macroporous wound-packing material. The plurality of micropores can have an average pore diameter. The average pore diameter of the micropores can be less than or equal to about 90 µm, less than or equal to about 75 µm, or less than or equal to about 50 µm.

The term "microcorrugated", as used herein, refers to a material that; in a dry, relaxed state; has a surface shape that includes alternate ridges and grooves.

The term "microporous layer", as used herein, refers to a material that has first and second major surfaces and a plurality of pores extending from the first major surface to the second major surface, the plurality of pores having an average pore diameter of less than or equal to about 90 µm. The first and second major surfaces may be substantially identical or may be substantially nonidentical.

The terms "comprises" and variations thereof do not have a limiting meaning where these terms appear in the description and claims.

As used herein, "a," "an," "the," "at least one," and "one or more" are used interchangeably. Thus, for example, a layer can be interpreted to mean "one or more" layers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
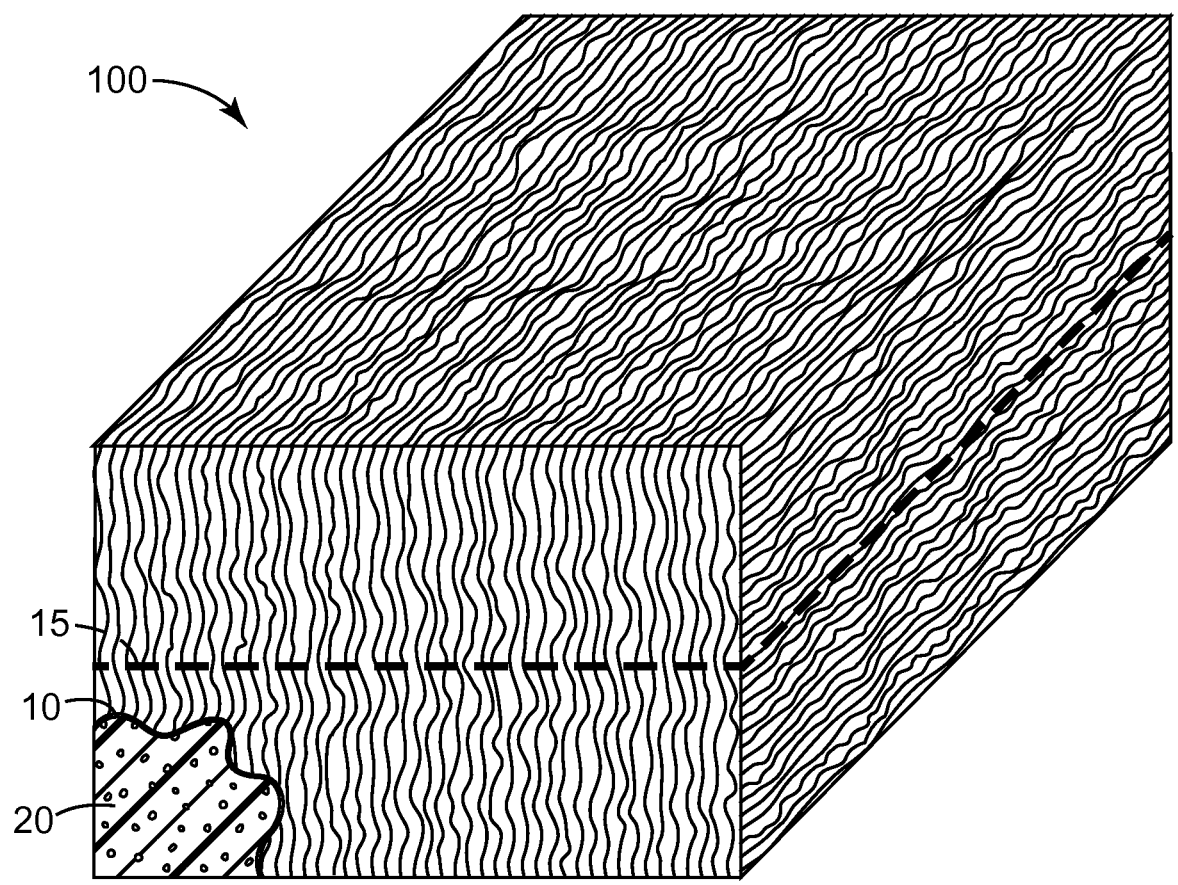
FIG. 1 is a perspective view of one embodiment of an article to facilitate wound healing according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to a method of wound therapy and an article for use in said method. In particular, the present disclosure relates to a method that places a microcorrugated microporous layer in contact with the wound surface, a macroporous wound-packing material adjacent the microporous layer, and a liquid-impermeable drape over said wound surface, microcorrugated microporous layer and wound-packing material. A source of negative pressure is placed into fluidic communication with the wound-packing material, thereby urging the wound surface against the microcorrugated microporous layer and drawing liquid (e.g., biological fluids) through the tissue and away from the wound surface. The inventive article of the present disclosure can be employed in the method to provide both the microcorrugated microporous layer and the macroporous wound-packing material arranged so that both can be applied to the wound surface simultaneously in the proper orientation.

It is now known that existing wound-packing materials that are used in conjunction with negative-pressure therapy have adverse effects that are related to their design. The present investigators found that documented problems filed with the U.S. Food & Drug Administration included, for example, a report indicating wound-packing material was stapled into the wound bed and required surgical removal, a report indicating wound-packing material (white foam) was left in a wound, reports that wound-packing material (foam) could not be removed from a wound without surgical intervention, reports that fragments of foam material adhered to wound surfaces aggressively enough to remain attached to the wound when the foam wound-packing material was removed from the patient, a report that removal of foam wound-packing material from a wound site caused significant bleeding that required hospitalization, and reports that wound packing material could not be found in the wound and surgery was required to find and remove it. The inventive article and methods solve all of the aforementioned reported problems and, additionally, provide tissue growth-stimulating benefits that facilitate more-rapid healing than the articles and methods used in conventional negative pressure wound therapy.

The microcorrugated microporous layer comprises a plurality of alternating ridges and grooves. In use, the grooves provide empty space into which new tissue can grow. Advantageously, the grooves can facilitate growth of relatively long (e.g., 0.5-10.0 cm), uninterrupted tracts of granulation tissue at the wound surface. In addition, the pore size (e.g., less than or equal to about 90 μm diameter) of the microporous layer substantially resists growth of granulation tissue into and/or through the pores, thereby minimizing the disruption of the new tissue when the microporous layer (or article) is removed at the end of the treatment. Manufacturer's guidelines for the use of contemporary articles (e.g., foam articles) in negative-pressure wound therapy currently recommend the articles should be removed from the wound bed, and optionally replaced, within 3 days of application. This restriction is placed on the current treatments in order to reduce the growth of new tissue into the article that could be damaged when the articles are removed. In contrast, because the microcorrugated microporous layer comprises pores that are dimensioned so that they substantially prevent growth of new tissue into or through the layer, the articles and methods of the present disclosure permit longer (>3-day) treatment times without increasing the risks associated with tissue-in-growth. Advantageously, this permits less maintenance by health care workers and improved recovery times while lowering health care cost.

Granulation tissue is formed on the surface of wounds that are actively healing. Formation of granulation tissue involves the migration of cells into the wound area. Granulation tissue comprises connective tissue that includes cells (e.g. fibroblasts), fibers (e.g., collagenous fibers, elastic fibers, and reticular fibers), and extracellular matrices (e.g., interstitial matrix, polysaccharides, proteins, and basement membranes). In addition, granulation tissue comprises vascular capillaries that supply oxygen, nutrients and leukocytes to the healing wound and remove cellular wastes to stimulate the healing processes.

The formation and maintenance of healthy granulation tissue correlates with successful wound healing. Accordingly, protocols for wound care such as, for example, maintaining moist wound environments, are designed to facilitate formation and maintenance of granulation tissue. However, in some situations, the buildup of excess tissue fluid in a wound bed can lead to tissue maceration (i.e., softening and wearing-away of the granulation tissue). Thus, negative-pressure wound therapies have been developed to remove excess fluid from the wound area.

Negative pressure wound therapies generally involve the use of a vacuum bandage to form a seal (e.g., via a pressure-sensitive adhesive layer) between a liquid-impermeable cover and the skin surrounding a wound site. Typically, the vacuum bandage is a bandage having a cover which seals about the outer perimeter of the wound and under which a vacuum is established to act on the wound surface. This vacuum applied to the wound surface facilitates healing of chronic wounds. Typically, suction tubes are provided for drawing away exudate from the wound, and this suction may be used to create the vacuum under the cover. If the cover is a flexible cover, which is typically more comfortable for the patient, some sort of porous wound-packing may be provided under the cover to provide the space in which the vacuum is formed. Vacuum treatment bandages and devices are disclosed in U.S. Pat. Nos. 6,095,992; 6,080,189; 6,071,304; 5,645,081; 5,636,643; 5,358,494; 5,298,015; 4,969,880; 4,655,754; 4,569,674; 4,382,441; and 4,112,947; which are all incorporated herein by reference in their entirety.

As shown, for example, in U.S. Pat. No. 5,645,081; a method of treating tissue damage is provided by applying negative pressure to a wound. The negative pressure is provided in sufficient duration and magnitude to promote tissue migration in order to facilitate the closure of the wound. An open cell polyester foam section covers the wound surface, a flexible hollow tube is inserted into the foam section at one end and attached to a vacuum pump at another end, and an adhesive sheet overlays the foam section and tubing and adheres to the skin surrounding the wound in order to form a seal that allows the creation of a vacuum when the suction pump is operating.

Lockwood et al. (International Publication No. WO 03/045492) disclose a thin, flexible member for use in a vacuum bandage is provided. The member includes a wound contacting surface configured to be in contact with and conform to a wound surface of a wound. The member further includes a plurality of discrete holes formed in the wound contacting surface, a port which communicates with the vacuum source, and communicating means between the holes and the port. The member is made from a generally incompressible material. Further, the incompressible material is generally transparent and non-porous.

It is now known that wound healing can be facilitated by contacting a microcorrugated, microporous layer against a wound surface and urging (e.g., via negative pressure) the wound surface against the layer. Without being bound by theory, it is believed the unique microcorrugated structure provides pressure points (i.e., ridges) that stimulate tissue growth in a manner similar to that described in Kane et al. ("Controlled induction of distributed microdeformation in wounded tissue via a microchamber array dressing"; J. Biomed. Mat. Res.; 95A:333-340; which is incorporated herein by reference in its entirety) and void spaces (i.e., grooves) into which the tissue can grow. Advantageously, the relatively long (e.g., 0.5 cm-25 cm), uninterrupted grooves can facilitate growth of relatively long, uninterrupted tracts of new tissue in a healing wound.

In one aspect, the present disclosure provides an article. The article can be used in a method of treating a wound. In any embodiment, the method may comprise the application of negative pressure to the article in order to facilitate healing of the wound. FIG. 1 shows one embodiment of an article 100 according to the present disclosure. The article 100 has a rectangular parallelepiped shape and comprises a microcorrugated microporous wound-contact layer 10 substantially surrounding a macroporous wound-packing material 20. In any embodiment, the macroporous wound-packing material 20 is less flexible than the microporous layer 10 and substantially defines the shape of the article 100. Also shown in FIG. 1 is an optional seam 15 that can be used to secure edges of the microporous layer 10 and, optionally, couple the microporous layer 10 to the underlying macroporous wound-packing material 20. In any embodiment, the seam 15 can comprise a filamentous material (e.g., polyester thread), an adhesive, a heat bond (e.g., ultrasonic bond) an adhesive tape, a staple, a clamp, or the like.

Figure 2:
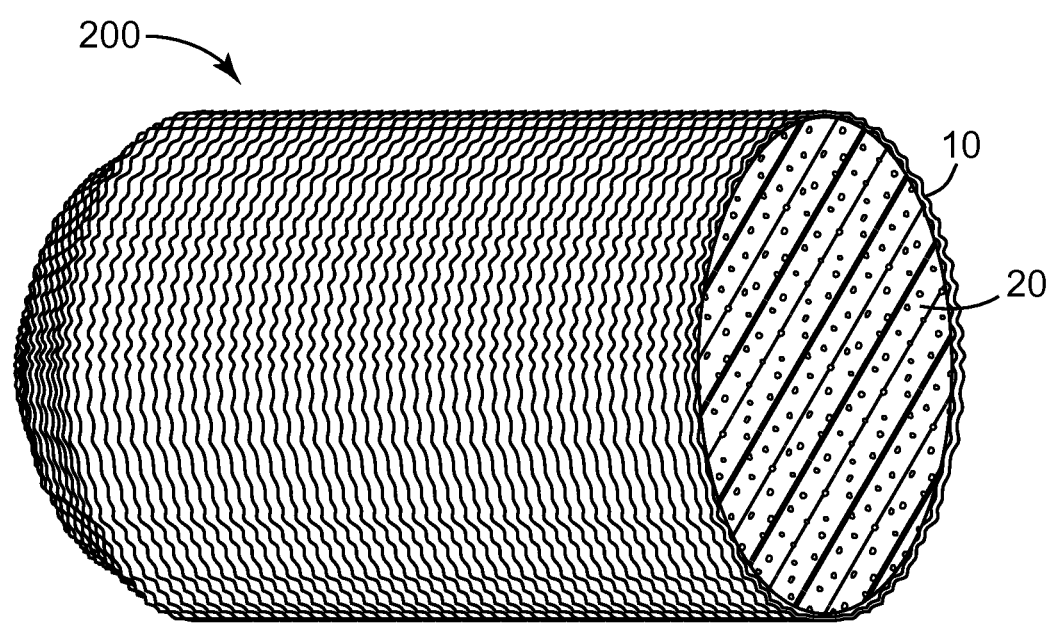
FIG. 2 is a perspective view, partially in section, of another embodiment of an article to facilitate wound healing according to the present disclosure.

FIG. 2 shows an alternative embodiment of an article 200 according to the present disclosure. The article 200 has a cylindrical shape and comprises a microcorrugated microporous wound-contact layer 10 and a macroporous wound-packing material 20. At each end of the cylindrical shape, the microporous wound contact layer 10 can be gathered (e.g., by crimping or twisting) and tied (not shown) or it can be secured with a seal as described above for the article 100 of FIG. 1.

Figure 3:
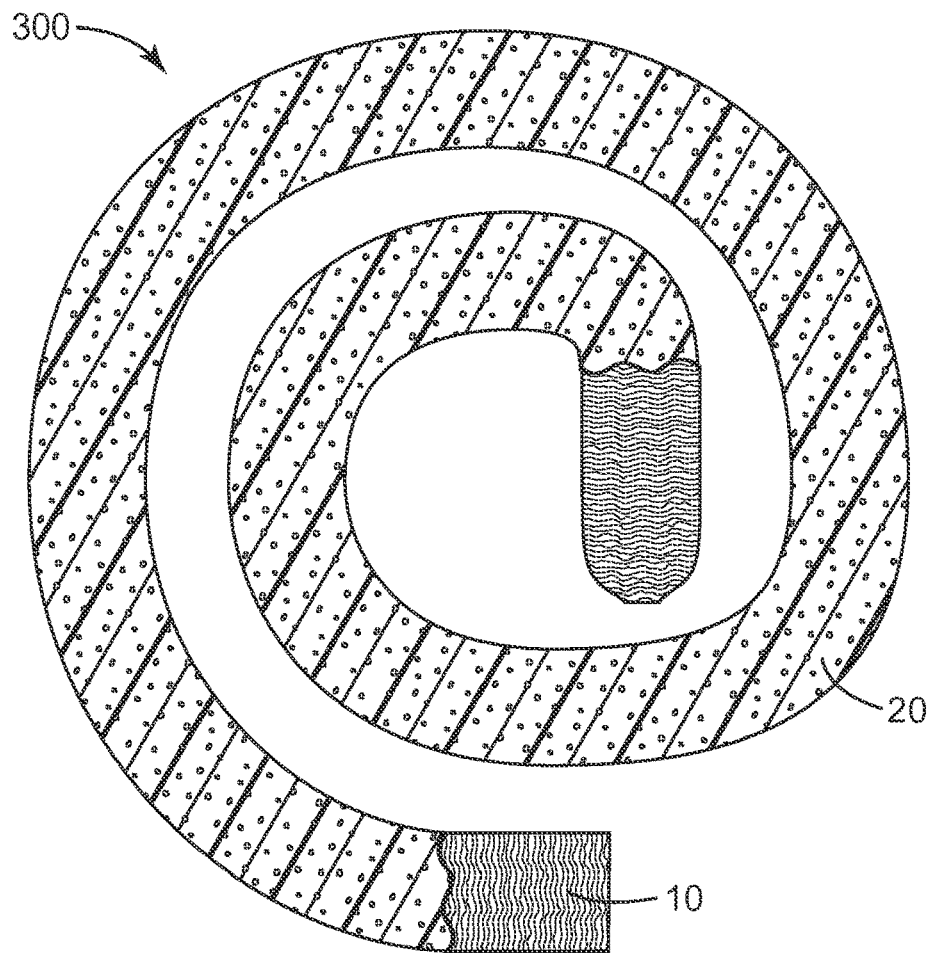
FIG. 3 is a plan view, partially in section, of an article to facilitate wound healing, the article having an extended longitudinal dimension.

FIG. 3 shows a plan view, partially in section, of an article 300 having an extended longitudinal dimension (length). The article 300 comprises a microcorrugated microporous wound-contact layer 10 and macroporous wound-packing material 20, as described herein. The wound-contact layer 10 comprises a plurality of alternating ridges 12 and grooves 14, as shown in detail in FIG. 4. In any embodiment, the ridges and grooves all extend in substantially a similar direction (e.g., they may be substantially parallel). In any embodiment, the ridges and grooves can extend substantially along a longitudinal axis of the article. In any embodiment, the ridges and grooves can extend in a direction that is substantially perpendicular to a longitudinal axis of the article.

In any embodiment, an article of the present disclosure is dimensioned for positioning in a wound bed. For example, in any embodiment, the article can be dimensioned for positioning in a superficial wound bed. In these embodiments, the article may have a surface having an area that is smaller, larger, or approximately the same area as the wound to be treated. Accordingly, it is contemplated that the article of the present disclosure may be provided in a variety of sizes and shapes (e.g., parallelepiped shapes, such as the rectangular parallelepiped shape illustrated in FIG. 1; and cylindrical shapes, such as the right circular cylinder shape illustrated in FIG. 2).

In any embodiment, articles of the present disclosure can have a length of at least about 1 cm, at least about 2 cm, at least about 3 cm, at least about 4 cm, at least about 5 cm, at least about 10 cm, at least about 15 cm, at least about 20 cm, at least about 25 cm, at least about 30 cm, at least about 35 cm, at least about 50 cm, or at least about 100 cm. Articles having an extended length can be positioned inside wounds using as much of the length as necessary to fill the wound cavity. Any excess length, if present, can simply be cut off using scissors or a scalpel, for example, before a cover (e.g., a liquid-impermeable drape) is applied to cover the article and the wound surface. In addition to the shapes of the articles shown in FIGS. 1-3, it is contemplated that an article of the present disclosure may be provided in the shape of a disc, a wedge, a frustum, a cone, a sphere, or a torroid, for example.

In any embodiment, the wound-contact layer 10 is a microcorrugated, microporous layer. The wound-contact layer 10 comprises a plurality of pores (not shown) that extend through the layer. Each pore in the microporous layer 10 has a pore diameter. It is desirable that the pore diameter is not large enough for sufficient growth of the tissue into and/or through the microporous layer to cause significant bonding (e.g., by entanglement of the tissue with the microporous material) between the healing tissue and the wound-contact layer 10. Such bonding can result in undesirable separation of substantial portions of the granulation tissue from the healing wound surface when the wound contact layer 10 is removed from the wound surface. Thus, in any embodiment, the average pore diameter of the plurality of pores in the microporous wound-contact layer is less than or equal to about 90 µm, less than or equal to about 70 µm, less than or equal to about 50 µm, or less than or equal to about 25 µm.

In any embodiment, the microporous wound-contact layer 10 may comprise a fabric. In any embodiment, the fabric may comprise a woven or knit fabric with pores that, optionally, have substantially uniform dimensions. Methods of making woven fabrics are well-known in the art. In any embodiment, the microporous wound-contact layer 10 may comprise a thermoplastic material (e.g., nylon, polyester). In any embodiment, the microporous wound-contact layer 10 is conformable. In any embodiment, the microporous wound-contact layer 10 is moderately-conformable to highly-conformable. Conformability can be measured, for example, using Method Number D 1388-96 Option B (Standard Test Method for Stiffness of Fabrics" (ASTM International), which is incorporated herein by reference in its entirety. In any embodiment, the stiffness of a 6"×8" sheet of the fabric can be less than or equal to about 10 Newtons when measured according to ASTM Method D 1388 Option B. In any embodiment, the stiffness of a 6"×8" sheet of the fabric is less than or equal to about 5 Newtons when measured according to ASTM Method D 1388 Option B. In any embodiment, the stiffness of a 6"×8" sheet of the fabric is less than or equal to about 2 Newtons when measured according to ASTM Method D 1388 Option B. In any embodiment, the stiffness of a 6"×8" sheet of the fabric is less than or equal to about 1 Newton when measured according to ASTM Method D 1388 Option B. In a preferred embodiment, the stiffness of a 6"×8" sheet of the fabric is about 0.8 Newton when measured according to ASTM Method D 1388 Option B.

In a preferred embodiment, the material used for the wound contact layer 10 is not substantially degraded by a sterilization process. A nonlimiting example of a suitable microporous wound-contact layer for use in an article of the present disclosure is the woven, nylon fabric used in 3M TEGADERM Non-Adherent Contact Layer (3M Company, St. Paul, Minn.). In any embodiment, the microporous wound-contact layer 10 is conformable. In any embodiment, the microporous wound-contact layer 10 is highly-conformable.

In any embodiment, the microporous wound-contact layer 10 may comprise a material (e.g., an ink, a dye) that is radiodense, relative to the wounded tissue (i.e., the material will substantially inhibit the passage of electromagnetic radiation and, thus will be visually distinguishable in an X-ray image.

The microporous wound-contact layer 10 is microcorrugated and, thus, comprises a plurality of alternating ridges and grooves. Suitable materials for the wound contact layer 10 are materials that retain the microcorrugations when exposed to conditions typically found in a wound site. For example, the layer 10 retains the microcorrugated structure when wet (e.g., when in contact with biological fluids in a wound site). In addition, the layer 10 retains the microcorrugations when exposed to a temperature typically found on the surface of skin or in deeper tissues (e.g., about 32-41° C.) and/or when exposed to negative pressures typically used in the treatment of wound sites.

Figure 4:
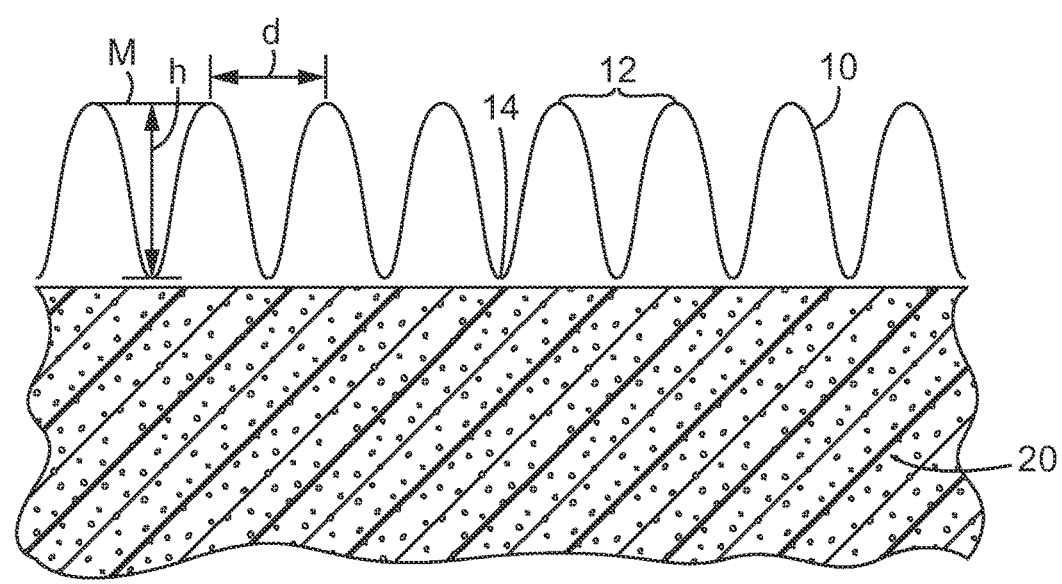
FIG. 4 is a detail cross-sectional side view of a portion of the article of FIG. 1A.

Prior to use (i.e., in ambient conditions), the microporous wound-contact layer 10 of the article 100 exists in a substantially dry, relaxed state. In the dry, relaxed state, the microporous wound-contact layer 10 comprises a plurality of alternating ridges 12 and grooves 14. Referring to FIG. 4; in the dry, relaxed state, there exists predetermined distance "d" between adjacent ridges 12. The distance d is predetermined by the conditions used to microcorrugate the material, as described herein. In any embodiment, the distance d between adjacent ridges is about 0.4 mm to about 5.0 mm.

In addition, each groove 14 of the plurality of groves has a predetermined depth that is measured along a line "h" that is perpendicular to a line "M" extending from adjacent ridges to the nadir of the groove between the adjacent ridges. In any embodiment, the depth h is about 0.2 mm to about 2 mm.

The microporous material that makes up the microporous wound contact layer 10 can be corrugated using equipment and processes that are known by a person having ordinary skill in the art. Equipment and processes for corrugating sheet materials are described, for example in U.S. Pat. No. 1,764,676; which is incorporated herein by reference in its entirety.

In any embodiment, an article of the present disclosure comprises a macroporous wound-packing material 20. The macroporous wound packing material 20 comprises pores that function as conduits to transport biological fluids through the article. Typically, the pores do not have a uniform pore diameter. However, wound-packing material having pores that have uniform-size diameters are acceptable. In any embodiment, the macroporous wound-packing material comprises pores having a pore diameter that is about 200 µm to about 5000 µm.

The macroporous wound-packing material 20 may serve to passively absorb or adsorb a bodily fluid (e.g., blood, tissue edema) secreted at the wound surface (not shown) and/or a treatment fluid (e.g., a lavage) applied to the wound site and/or wound dressing. The macroporous wound-packing material 20 further serves as a conduit for the passage of liquid (e.g., wound exudates from tissue edema) away from the wound surface to a suitable collection site (e.g., a liquid trap, a container and/or absorbent material that is in fluidic communication with the wound surface and a source of negative pressure (not shown)). In any embodiment, wound exudate can also flow around the exterior sides of the article toward a source of negative pressure.

Preferably, each groove 14 of the plurality of grooves has a longitudinal dimension that is relatively long (e.g., >0.5 cm), thereby permitting growth of relatively long, uninterrupted tracts of new tissue at the wound surface. In any embodiment, each groove of the plurality of grooves extends at least 0.5 cm. In any embodiment, each groove of the plurality of grooves extends at least 1.0 cm. In any embodiment, each groove of the plurality of grooves extends at least 1.5 cm. In any embodiment, each groove of the plurality of grooves extends at least 2.0 cm. In any embodiment, each groove of the plurality of grooves extends at least 3.0 cm. In any embodiment, each groove of the plurality of grooves extends at least 5.0 cm. In any embodiment, each groove of the plurality of grooves extends greater than 5.0 cm. In any embodiment, each groove of the plurality of grooves extends about 0.5 cm-10.0 cm, inclusive. In any embodiment, each groove of the plurality of grooves extends about 0.5 cm-25.0 cm, inclusive.

In any embodiment, the macroporous wound packing material 20 comprises open-cell foam. In any embodiment, the macroporous wound packing material 20 comprises compressible open-cell foam. Preferably, the open-cell foam is compressed when subjected to negative pressures that are typically used in wound treatment therapy (e.g., negative pressures between about −20 Torr to about −300 Torr, inclusive). In any embodiment, the open-cell foam can be compressed (under negative pressures between about −20 Torr to about −300 Torr, inclusive) to an extent that decreases at least one lineal dimension to about 50% of its magnitude compared to the lineal dimension when the article exists in its dry, relaxed state (i.e., compared to the lineal dimension when the article is held in ambient conditions of temperature, relative humidity, and pressure). In a preferred embodiment, the open-cell foam can be compressed (under a negative pressure of about −125 Torr) to an extent that decreases at least one lineal dimension by at least about 85% of its magnitude compared to the lineal dimension when the article exists in its dry, relaxed state (i.e., compared to the lineal dimension when the article is held in ambient conditions of temperature, relative humidity, and pressure). In any embodiment, the open-cell foam comprises reticulated polyurethane foam. In any embodiment, the material used for the macroporous wound-packing material 20 is not substantially degraded by a sterilization process.

In any embodiment, the macroporous wound-packing material 20 may comprise a material (e.g., an ink, a dye) that is radiodense, relative to the wounded tissue (i.e., the material will substantially inhibit the passage of electromagnetic radiation and, thus will be visually distinguishable in an X-ray image.

In any embodiment, an article of the present disclosure further comprises an active agent (not shown). The active agent can directly or indirectly facilitate wound healing. In any embodiment, the active agent is disposed on and/or in the microporous layer 10. Alternatively or additionally, in any embodiment, the active agent is disposed on and/or in the macroporous wound-packing material 20. In any embodiment, the active agent may be released (e.g., within a predetermined period of time) from the microporous wound-contact layer and/or the wound-packing material. The active agent can be any active agent (e.g., material and/or compound) that facilitates growth of granulation tissue in a wound bed. Non-limiting examples of suitable active agents include an antimicrobial agent (e.g., a bactericidal composition, a bacteriostatic composition, an antifungal composition, and an antiviral composition), a growth factor, an angiogenic factor, an anesthetic, a mucopolysaccharide, a protein, an adjuvant, a nitric oxide (NO)-releasing composition, and a combination of any two or more of the foregoing active agents.

The active agent can be deposited into and/or onto the microporous layer 10 using any suitable process such as, for example, dip-coating, or spray-coating. A person having ordinary skill in the art will recognize a suitable process for applying a particular active agent to the microporous layer while maintaining its porosity and microcorrugations.

Figure 5:
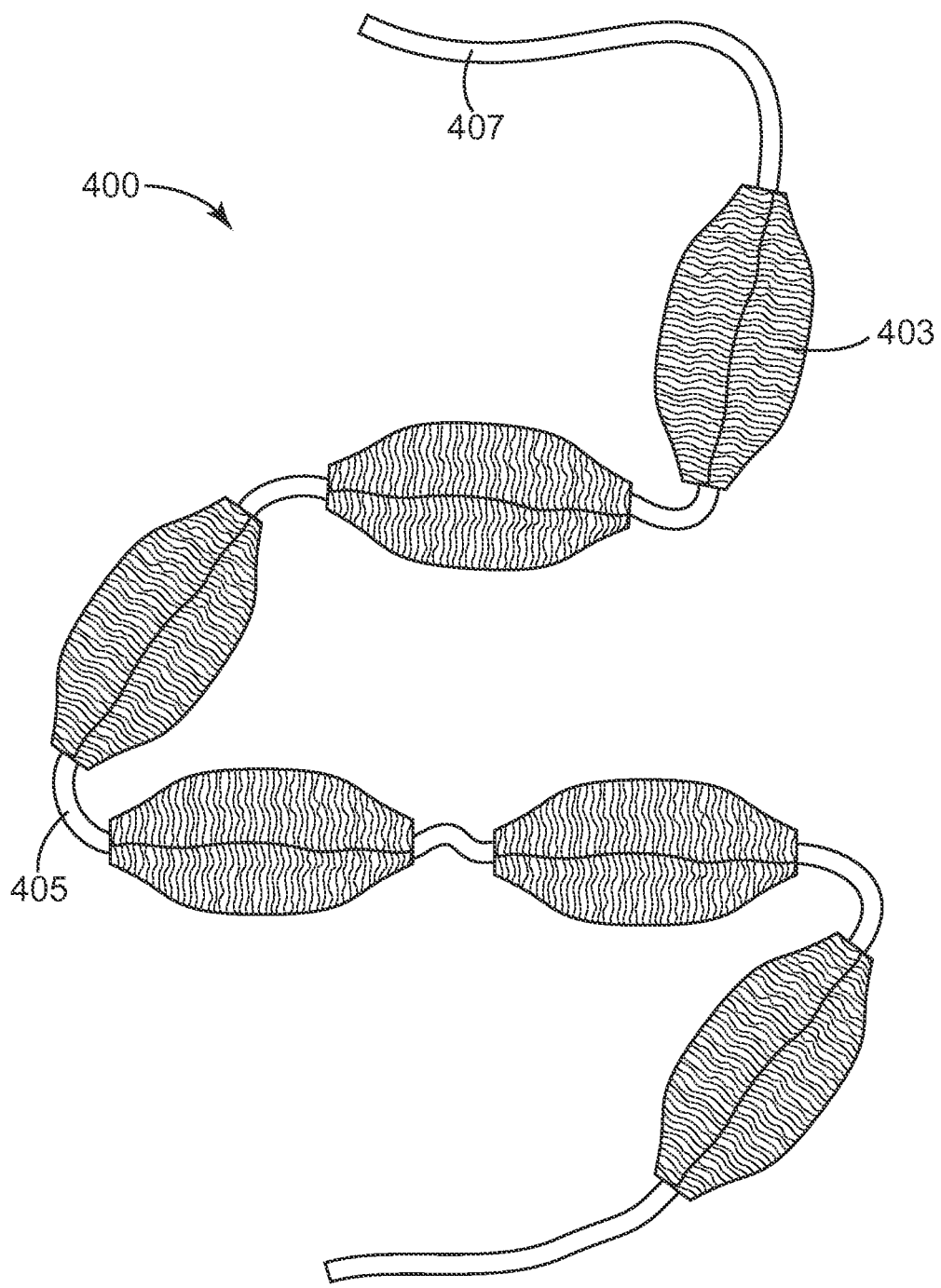
FIG. 5 is a plan view of one embodiment of an article comprising a plurality of connected segments according to the present disclosure.

In another aspect, the present disclosure provides an article comprising a plurality of segments. FIG. 5 shows a plan view, partially in section, of one embodiment of the article 400 comprising a plurality of segments 403 according to the present disclosure. Each segment 403 comprises a macroporous wound-packing material coupled to a microcorrugated microporous wound-contact layer according to any embodiment disclosed herein and a macroporous wound-packing material according to any embodiment disclosed herein. The macroporous wound-packing material 20 is substantially enveloped in the microcorrugated microporous wound-contact layer 10. The microporous layer 10 comprises a plurality of pores, the plurality having an average pore diameter, wherein the average pore diameter is less than or equal to about 90 µm, less than or equal to about 70 µm, less than or equal to about 50 µm, or less than or equal to about 25 µm. Optionally, at least one of the segments 403 further may comprise a seam (not shown), as described herein.

Each of the segments 403 is connected to at least one other segment via a tether 405. In any embodiment, the tether 405 comprises a conformable material (e.g., a filamentous material such as a thread, a ribbon, a string, or the like). A non-limiting example of a suitable material for a tether 405 is a CURITY Plain Packing Strip (¼"×15') obtained from Covidien (Mansfield, Mass.). In a preferred embodiment, the material used for the tethers 405 is not substantially degraded by a sterilization process.

The tether can be coupled to a segment 403 by a variety of means including, but not limited to; forming a knot with the microporous layer material; tying a knot around the microporous layer material; tying a knot around the segment 403; or securing the tether to the microporous layer material and/or wound packing material via a stitch, a staple, a clamp, an adhesive, an adhesive tape.

In any embodiment, the tether 405 may comprise a material (e.g., an ink, a dye) that is radiodense, relative to the wounded tissue (i.e., the material will substantially inhibit the passage of electromagnetic radiation and, thus will be visually distinguishable in an X-ray image.

In any embodiment, the article 400 further can comprise an extraction element 407. The extraction element can be secured (e.g., as described above for the tether 405) to one of the terminal segments 403 of the article 400, as shown in FIG. 4. In any embodiment, the extraction element 407 can comprise the same material as the tether 405. In any embodiment, the extraction element 407 can comprise a material that is visually distinguishable from the tether 405.

In use, the article 400 comprising the plurality of segments 403 can be cut (e.g., by severing one of the tethers with a scissors or a scalpel) to a length with a sufficient number of segments to fill a particular wound surface or wound cavity. Advantageously, the article 400 can be cut before filling the wound cavity or after filling the wound cavity. The article is particularly useful in treating a wound with a relatively small opening, the wound extending into the body under the skin, for example (e.g., an "undermining" or "tunneling" wound). In these embodiments, the individual segments can be introduced into the wound opening and urged further into the wound with the next segment until the wound cavity is filled. After filling the wound cavity, any additional segments 403, if present, protruding from the wound cavity can be severed from the article 400. In these embodiments, a person having ordinary skill in the art will recognize that severing one or more segments from the article can result in the creation of an extraction element from the tether that has been severed.

Figure 8:
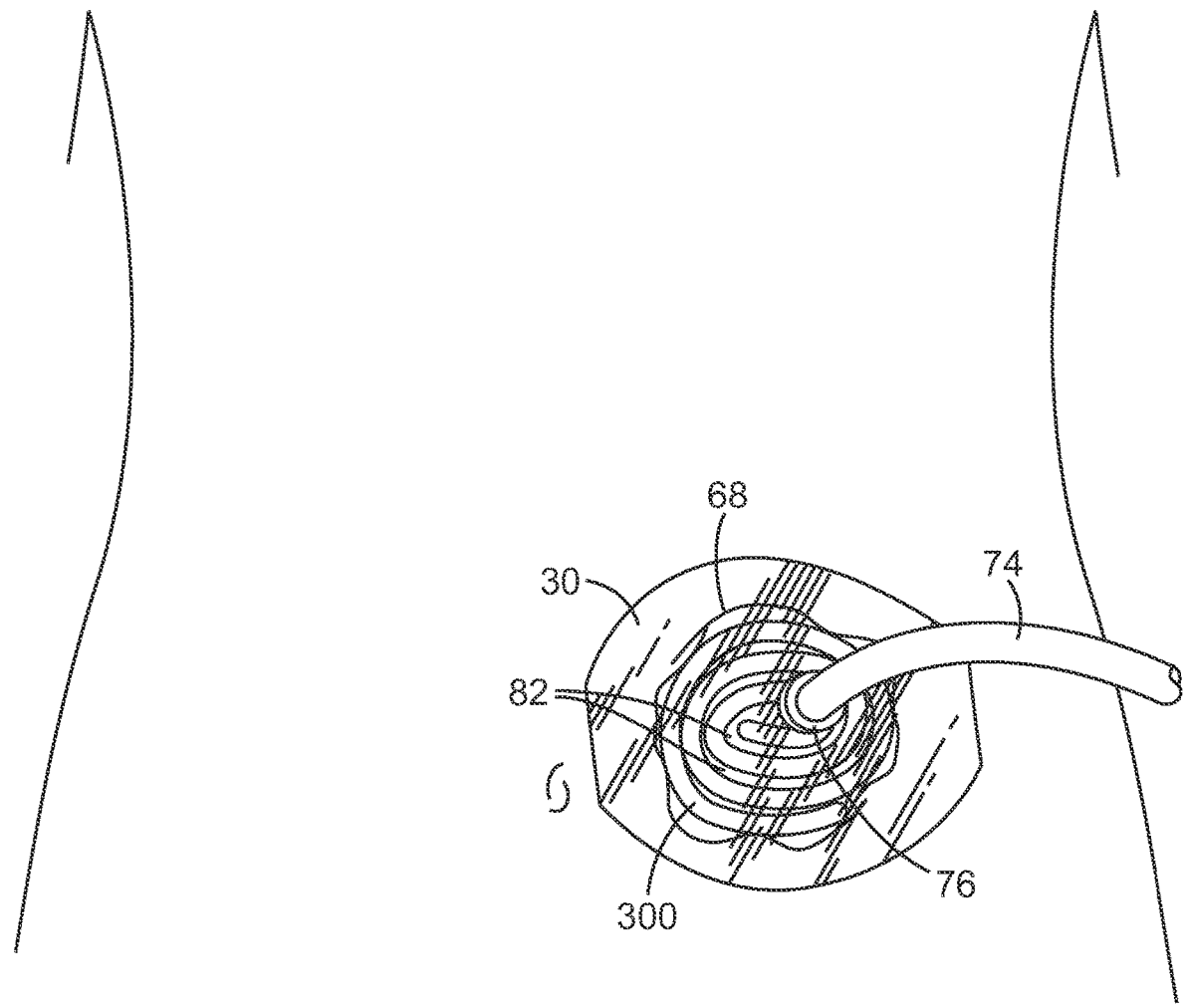
FIG. 8 is a perspective view of a wound treatment site with an article of the present disclosure disposed in an operable position proximate the wound surface.

In any embodiment, when an elongated article (e.g., article 300 or article 400) of the present disclosure is placed into a wound (e.g., by coiling, as shown in FIG. 8, or by randomly packing (not shown)), channels are formed between adjacent portions of the article in the wound (see FIG. 8). Advantageously, these channels provide additional paths for wound exudate to be transported away from the wound site under negative pressure. Thus, both the article and the channels facilitate the movement of biological fluids away from the wound site.

In yet another aspect, the present disclosure provides a kit. In an embodiment, the kit comprises any article comprising a macroporous wound-packing material and a microcorrugated microporous wound-contact layer, according to the present disclosure. In any embodiment, the article is dimensioned for positioning in a wound bed, as discussed herein.

In another embodiment, the kit comprises a microcorrugated microporous layer comprising a plurality of micropores, the plurality having an average pore diameter, wherein the average pore diameter of the micropores is less than or equal to about 90 µm; and a macroporous wound-packing material, as described hereinabove. In any embodiment, the average pore diameter of the micropores of the microporous layer is less than or equal to about 70 µm, less than or equal to about 50 µm, or less than or equal to about 25 µm.

In any embodiment of a kit, the kit further comprises instructions for using the microcorrugated microporous layer, the macroporous wound-packing material and/or the article of the present disclosure. In any embodiment of a kit, the kit further comprises a liquid-impermeable drape. In any embodiment of a kit, the kit further comprises the liquid-impermeable drape comprises a valve. In any embodiment of a kit, the microporous layer comprises a plurality of alternating ridges and grooves; wherein the plurality of the ridges have a distance between adjacent ridges; wherein, in a relaxed, dry state, an average distance between adjacent ridges of the plurality of ridges is about 0.4 mm to about 5.0 mm. In any embodiment of a kit, the microporous layer comprises a plurality of alternating ridges and grooves, each groove having a depth; wherein, in a relaxed, dry state, the depth is about 0.2 mm to about 2 mm.

Figure 6:
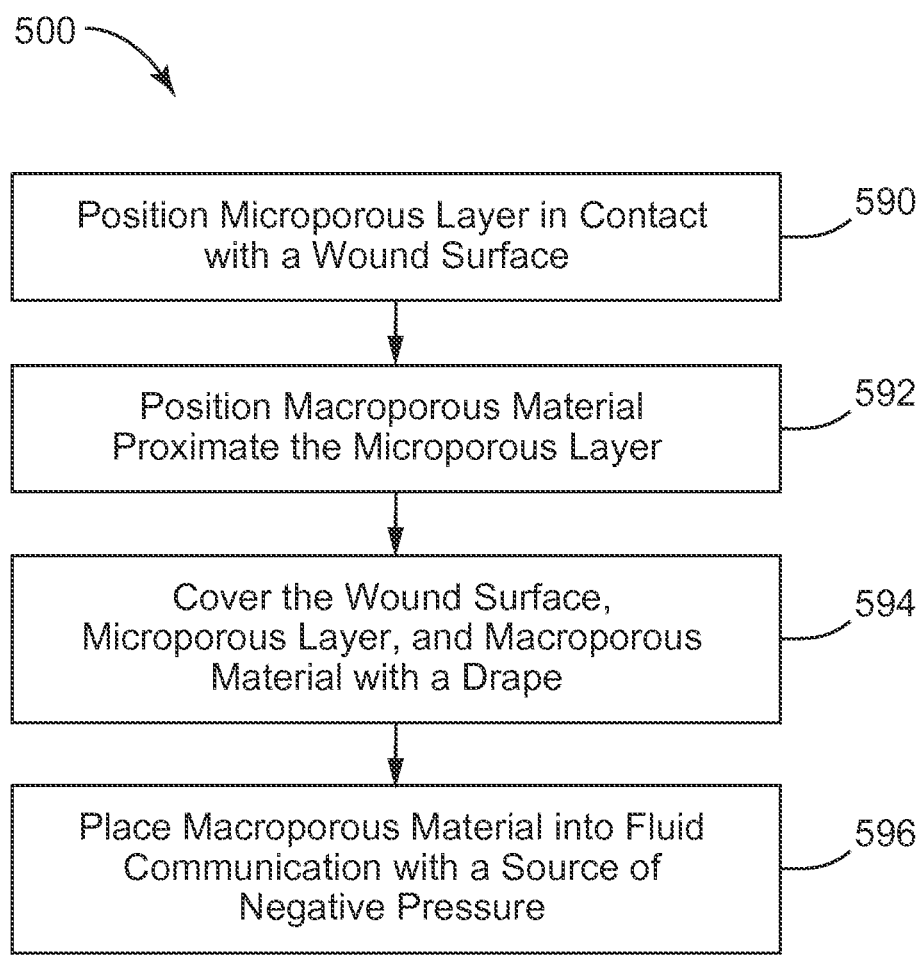
FIG. 6 is a block diagram of one embodiment of a method of treating a wound according to the present disclosure.

In yet another aspect, the present disclosure provides a method. The method can be used to treat a wound. FIG. 6 shows a block diagram of one embodiment of a method 500 for treating a wound according to the present disclosure. The method 500 comprises the step 590 of positioning a first major surface of a microcorrugated microporous layer in contact with a wound surface of a wound bed. The microporous layer is dimensioned, and optionally shaped, for positioning against the wound bed, as described herein. The microporous layer comprises a plurality of micropores, the plurality having an average pore diameter, wherein the average pore diameter of the micropores is less than or equal to about 90 µm, less than or equal to about 70 µm, or less than or equal to about 50 µm.

The method 500 further comprises the step 592 of positioning a macroporous wound-packing material proximate a second major surface of the microporous layer. The macroporous material can be any suitable macroporous material described herein. Positioning the macroporous material proximate the microporous layer comprises positioning the microporous layer between the wound surface and the macroporous material. It is contemplated that steps 590 and 592 of method 500 may be accomplished simultaneously when an article (e.g., article 100 of FIG. 1, article 200 of FIG. 2, or article 300 of FIG. 3) according to the present disclosure is positioned in a wound bed.

Figure 7:
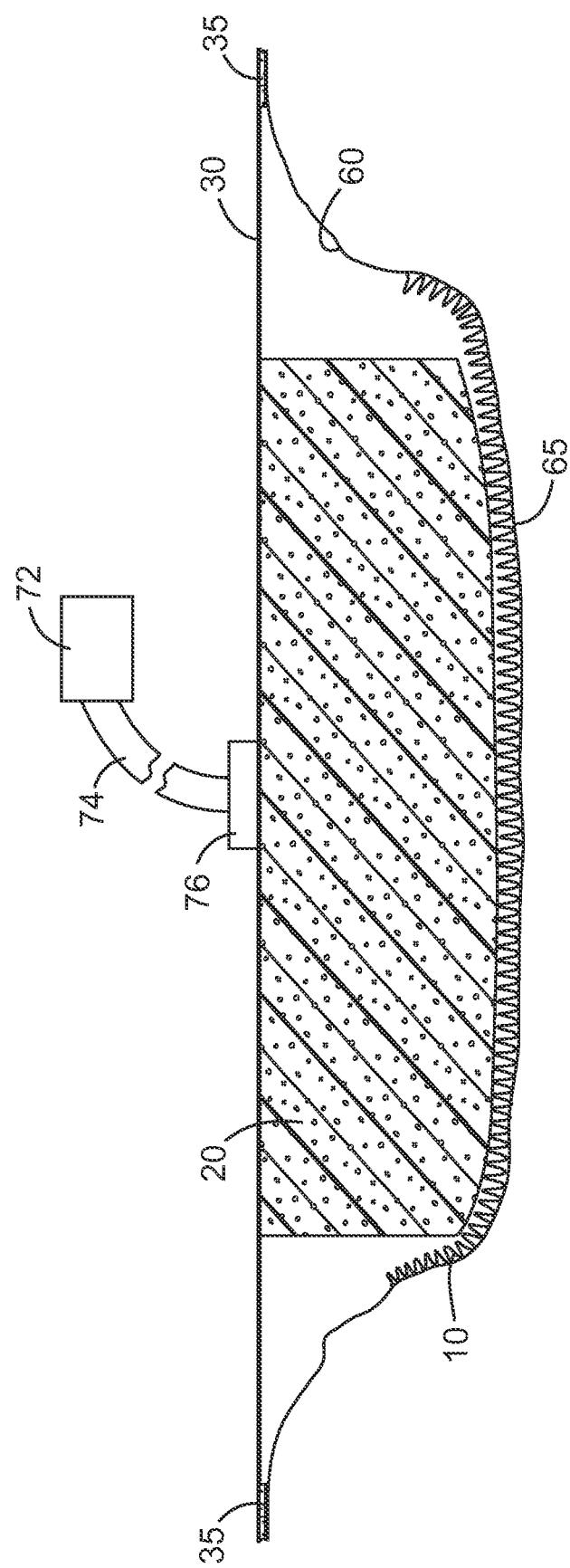
FIG. 7 is a cross-sectional side view of a wound site being treated with a microporous wound-contact layer, a macroporous material, and a liquid-impermeable drape; wherein the macroporous material is in fluidic communication with a source of negative pressure.

The method 500 further comprises the step 594 of covering the wound surface, the layer, and macroporous material with a liquid-impermeable drape. FIG. 7 shows a schematic cross-section view of a wound surface 65 in an area of skin 60 that is being treated according to an embodiment of the method after the completion of step 594. The microporous layer 10 is positioned in contact with the wound surface 65. Positioned proximate the microporous layer 10 is the macroporous wound-packing material 20. The microporous layer 10 is positioned between the wound surface 65 and the macroporous wound-packing material 20. Covering the skin 60, microporous layer 10, and macroporous wound-packing material 20 is a drape 30. Preferably, the drape 30 comprises an adhesive 35 (e.g., a pressure-sensitive adhesive disposed around the perimeter of the drape or optionally disposed under the entire drape) to form an adhesive seal between the skin and the drape. Alternatively, the edges of the drape 30 may be sealed to the skin by using a pressure-sensitive adhesive tape (not shown) to secure the perimeter of the drape to the skin. Thus, in any embodiment, covering the wound surface with a liquid-impermeable drape comprises adhering (e.g., either directly or indirectly) the liquid-impermeable drape to a patient surface (e.g., skin) proximate the wound surface.

The method 500 further comprises the step 596 of placing the macroporous wound-packing material 20 into fluid communication with a source of negative pressure (vacuum pump 72, FIG. 6). The macroporous wound-packing material 20 serves as a conduit to facilitate the movement of liquid (e.g., wound exudate) away from the wound surface. Placing the macroporous wound-packing material 20 into fluid communication with a source of negative pressure 72 can comprise, for example, passing a piece of tubing 74 connected to a vacuum source through the drape or under the drape into the space between the drape and the macroporous material. Alternatively, in any embodiment, the drape 30 may comprise a port 76 (e.g., optionally, a port with a valve), as shown in FIG. 6. In any embodiment, the port may be coupled to a source of negative pressure. When the port is coupled to a source of negative pressure, the macroporous material is placed into fluid communication with the source of negative pressure. In any embodiment, placing the wound area into fluid communication with a source of negative pressure comprises subjecting the wound area to a negative pressure that is selected for use in a wound therapy (e.g., a negative pressure of about −20 Torr to about −300 Torr).

In any embodiment of the method, the macroporous material is coupled to and/or substantially surrounded by the microporous layer (e.g., the macroporous material and the microporous layer are portions of an article according to the present disclosure). In these embodiments, positioning the first major surface of the microporous layer proximate a wound surface comprises simultaneously positioning the macroporous material proximate the wound surface, wherein the microporous layer is positioned between the wound surface and the macroporous material.

FIG. 8 shows an elongated article 300 of the present disclosure operationally positioned in a wound site 68. The article 300 and wound site 68 are covered with a transparent drape 30. The drape 30 comprises a port 76 connected to a tubing 74. The tubing 74 is in fluid communication with a source of negative pressure (not shown). Also shown in FIG. 8 is a channel 82 located between the coils of the article 300. The channel 82 functions to facilitate movement of biological fluids away from the wound surface when negative pressure is applied to the wound area via the port 76.

EXEMPLARY EMBODIMENTS

Embodiment A is an article comprising a macroporous wound-packing material coupled to a microcorrugated microporous wound-contact layer; wherein the microporous layer comprises a plurality of pores, the plurality having an average pore diameter; wherein the average pore diameter is less than or equal to about 90 µm.

Embodiment B is an article comprising a macroporous wound-packing material substantially enveloped in a microcorrugated microporous wound-contact layer; wherein the microporous layer comprises a plurality of pores, the plurality having an average pore diameter; wherein the average pore diameter is less than or equal to about 90 µm.

Embodiment C is the article of Embodiment A or Embodiment B, wherein the layer comprises a woven fabric or a knit fabric.

Embodiment D is the article of any one of the preceding Embodiments, wherein the microporous layer comprises nylon.

Embodiment E is the article of any one of the preceding Embodiments, wherein the wound-packing material is coupled to at least a portion of the layer.

Embodiment F is the article of any one of the preceding Embodiments; wherein the plurality of the ridges have a distance between adjacent ridges; wherein, in a relaxed, dry state, an average distance between adjacent ridges of the plurality of ridges is about 0.4 mm to about 5.0 mm.

Embodiment G is the article of any one of the preceding Embodiments, wherein the layer comprises a plurality of alternating ridges and grooves, each groove having a depth; wherein, in a relaxed, dry state, the depth is about 0.2 mm to about 2 mm.

Embodiment H is the article of Embodiment G, wherein the wound-packing material comprises open-cell foam.

Embodiment I is the article of any one of the preceding Embodiments, wherein the macroporous material comprises compressible open-cell foam.

Embodiment J is the article of Embodiment I, wherein the open-cell foam comprises reticulated polyurethane foam.

Embodiment K is the article of any one of the preceding Embodiments, wherein the macroporous material comprises pores having a pore diameter that is about 200 µm to about 5000 µm.

Embodiment L is the article of any one of the preceding Embodiments, wherein the wound-packing material comprises a major surface that faces the microporous layer, wherein at least a portion of the surface comprises a plurality of alternating ridges and grooves.

Embodiment M is the article of any one of the preceding Embodiments, further comprising an active agent disposed on and/or in the microporous layer.

Embodiment N is the article of Embodiment M, wherein the active agent is selected from the group consisting of an antimicrobial compound, a growth factor, an angiogenic factor, an anesthetic, a mucopolysaccharide, a protein, an adjuvant, a nitric oxide-releasing composition, and a combination of any two or more of the foregoing active agents.

Embodiment O is the article of any one of the preceding Embodiments, wherein the layer comprises a plurality of alternating ridges and grooves, each groove having a longitudinal dimension; wherein, in a relaxed, dry state, the longitudinal dimension extends at least about 0.5 cm.

Embodiment P is an article, comprising:
a plurality of segments, each segment comprising a macroporous wound-packing material substantially enveloped in a microcorrugated microporous wound-contact layer;
wherein the microporous layer comprises a plurality of pores, the plurality having an average pore diameter, wherein the average pore diameter is less than or equal to about 90 µm; and
a tether connecting a first segment to a second segment.

Embodiment Q is the article of Embodiment P, wherein the segments of the plurality of segments are connected in a linear array.

Embodiment R is the article of Embodiment P or Embodiment Q, wherein the plurality of segments comprises two terminal segments.

Embodiment S is the article of Embodiment R, further comprising an extraction element attached to at least one of the terminal segments.

Embodiment T is the article of any one of the preceding Embodiments, wherein the wound-contact layer, the wound-packing layer, and/or the tether, if present, comprises a material that is radiodense relative to wound tissue.

Embodiment U is a method, comprising:
positioning a first major surface of a microcorrugated microporous layer in contact with a wound surface of a wound bed;
wherein the microporous layer is dimensioned for positioning against the wound bed;
wherein the microporous layer comprises a plurality of micropores, the plurality having an average pore diameter; wherein the average pore diameter of the micropores is less than or equal to about 90 µm;

positioning a macroporous wound-packing material proximate a second major surface of the microporous layer;
   wherein positioning the macroporous material proximate the microporous layer comprises positioning the microporous layer between the wound surface and the macroporous material;
covering the wound surface, the layer, and macroporous material with a liquid-impermeable drape; and
placing the macroporous material into fluid communication with a source of negative pressure.

Embodiment V is the method of Embodiment U, wherein the macroporous material is coupled to and/or substantially surrounded by the microporous layer, wherein positioning the first major surface of the microporous layer proximate a wound surface comprises simultaneously positioning the macroporous material proximate the wound surface, wherein the microporous layer is positioned between the wound surface and the macroporous material.

Embodiment W is the method of Embodiment U or Embodiment V, wherein covering the wound surface with a liquid-impermeable drape comprises adhering the liquid-impermeable drape to a patient surface proximate the wound surface.

Embodiment X is the method of Embodiment W, wherein the wound surface comprises a wound periphery, wherein adhering the drape to the area comprises forming a liquid-impermeable seal outside the wound periphery.

Embodiment Y is the method of any one of Embodiments U through X, wherein the drape further comprises a port, wherein placing the macroporous material into fluid communication with a source of negative pressure comprises connecting a source of negative pressure to the port.

Embodiment Z is the method of any one of Embodiments U through Y, wherein placing the wound area into fluid communication with a source of negative pressure comprises subjecting the wound area to a negative pressure of about −20 Torr to about −300 Torr.

Embodiment AA is a kit comprising the article of any one of Embodiments A through T, wherein the article is dimensioned for positioning in a wound bed.

Embodiment BB is the kit of Embodiment AA, wherein the kit comprises a plurality of the articles.

Embodiment CC is the kit of Embodiment AA, wherein the article comprises plurality of segments, wherein each segment of the plurality of segments comprises the microcorrugated microporous layer and the macroporous wound-packing material, wherein the plurality of segments comprises a first segment and a second segment coupled to the first segment.

Embodiment DD is a kit, comprising:
a microcorrugated microporous layer comprising a plurality of micropores, the plurality having an average pore diameter; wherein the average pore diameter of the micropores is less than or equal to about 90 µm; and
a macroporous wound-packing material.

Embodiment EE is the kit of any one of Embodiments AA through DD, further comprising a liquid-impermeable drape.

Embodiment FF is the kit of Embodiment EE, wherein the liquid-impermeable drape comprises a normally-closed valve.

Embodiment GG is the kit of any one of Embodiments AA through FF, wherein the layer comprises a fabric.

Embodiment HH is the kit of Embodiment GG, wherein the fabric comprises a knit fabric.

Embodiment II is the kit of Embodiment GG or Embodiment HH, wherein the fabric comprises a thermoplastic material.

Embodiment JJ is the kit of Embodiment II, wherein the thermoplastic material comprises nylon.

Embodiment KK is the kit of any one of Embodiments AA through JJ, wherein the microporous layer comprises a plurality of alternating ridges and grooves; wherein the plurality of the ridges have a distance between adjacent ridges; wherein, in a relaxed, dry state, an average distance between adjacent ridges of the plurality of ridges is about 0.4 mm to about 5.0 mm.

Embodiment LL is the kit of any one of Embodiments V through FF, wherein the microporous layer comprises a plurality of alternating ridges and grooves, each groove having a depth; wherein, in a relaxed, dry state, the depth is about 0.2 mm to about 2 mm.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials.

Materials utilized in the preparation of the examples are shown in Table 1.

TABLE 1

| Materials Table | | |
| --- | --- | --- |
| Component | Description | Source |
| Microporous layer | 3M TEGADERM Non-Adherent Contact Layer; Part No. 5643 | 3M Health Care; St. Paul, MN |
| Wound-packing material | Open-cell polyurethane foam; Part number A30M | Crest Foam Industries, Inc. Moonachie, New Jersey |
| Tether | CURITY Plain Packing Strip (¼" × 15') | Covidien; Mansfield, MA |

Example 1. Preparation of an Article According to the Present Disclosure

A sheet of 3M TEGADERM Non-Adherent Contact Layer was subjected to a corrugating process similar to that described in U.S. Pat. No. 1,764,676; with the equipment and roller speeds set to form a microcorrugated sheet that; in a dry, relaxed state; had ridges that were approximately 1.5 mm apart and grooves that were approximately 0.7 mm deep (the depth being measured along a first line that is perpendicular to a second line extending from adjacent ridges to the nadir of the groove between the adjacent ridges; as described herein). The relaxed, dry microcorrugated sheet was cut to approximately 12 cm long×7.5 cm wide. The microcorrugations extended across the width of the sheet.

A cylindrical piece of open-cell polyurethane foam approximately 2.5 cm (diameter)×approximately 3 cm (length) was wrapped with the 12 cm long×7.5 cm microcorrugated sheet such that the ridges extended around the circumference of the cylinder and the cylinder was approximately centered in the sheet. The excess sheet material extending beyond both ends of the cylinder was twisted several times and secured with string or a rubber binder.

Example 2. Preparation of an Article Having a Plurality of Segments According to the Present Disclosure Six articles were prepared as described in Example 1. After twisting the microporous layers at both ends of each article, the twisted ends were tied using a tether (approximately 6 cm long) described in Table 1. Each tether was used to tie two separate articles. Thus, each tether linked two adjacent articles (i.e., segments) to form a single article comprising six segments that were linked end-to-end, as illustrated in FIG. 5.

Example 3. Effect of Packing Material on Wound Healing During Negative Pressure Treatment of Wounds A protocol similar to the one described in Borgquist et al. (Borgquist, O., Gustafsson, L., Ingemansson, R. et al. Tissue ingrowth into foam but not into gauze during negative pressure wound therapy. Wounds 2009; 21: 11, 302-309; which is incorporated herein by reference in its entirety) was used to evaluate the effect of an article having a microcorrugated microporous wound contact layer on wound healing. A full thickness porcine wound model previously developed for other wound dressings was used as a way to determine how well tissues granulate under negative pressure.

Four paraspinal wounds (2 per side) full thickness skin wounds, each wound measuring 4 cm in diameter, were surgically created in pigs with approximately 5 cm between wounds. Each wound was filled with a different material as listed in Table 2:

TABLE 2

Material used to pack the wound in each of the experiments.

| Experiment | Wound-packing Material |
| --- | --- |
| Control 1 - No tissue-contact layer | V.A.C. GRANUFOAM packing |
| Control 2 - Noncorrugated tissue contact layer | V.A.C. GRANUFOAM packing wrapped in TEGADERM Contact Layer |
| Example 3 | V.A.C. GRANUFOAM packing wrapped in microcorrugated TEGADERM Contact Layer |
| Control 3 - Traditional wound packing | CURITY gauze sponge |

All wound packings (dressings) were covered with KCI 1-2-Blue drape (from Kinetic Concepts, Inc.) and vacuum was applied at 125 mm Hg to all the sites. After 3 days dressings were removed and the wound tissue was photographed and visually observed. Good granulation was observed after 3 days in the Control 1 wound and granulation was partially observed in the Control 2 wound. In the wound treated according to Example 3, granulation tissue was observed to have a striated structure that mirrored the microcorrugated structure of the microcorrugated contact layer. In the Control 3 wound, granulation tissue was observed only in a portion of the wound.

After observing and photographing the wounds, each wound dressing was replaced with a dressing of the same type and the dressings were covered and vacuum was reapplied as described above. Four days later (i.e., 7 days after the wounds were created), the packing material was pulled from each of the wounds. A Force Gauge Model M5-50 (Series 5 Force Gauge) from Mark-10 (Copiague, N.Y.) was used to determine the amount of force needed to remove the wound packing using a pair of forceps. The instantaneous force readout is shown on the display but the peak value is recorded accordingly. Removal of the packing from each wound was videotaped. The results of the observations at Day 3 and Day 7 are summarized in Table 3. Visual evaluation of the wound tissue was not practical on day 7 because the force measurement resulted in removal of portions of the tissue in at least some of the wounds.

TABLE 3

Appearance of wound tissue after 3 days of negative-pressure therapy and the amount of force required to remove the wound-packing material after 7 days of negative-pressure therapy.

| Wound Packing | Tissue Granulation (Day 3) | Force Required (Day 7) to Remove Packing |
| --- | --- | --- |
| Control 1 - No tissue-contact layer | Very good granulation and observed to replicate texture of foam | 5.19 lbf, 5.60 lbf, and 5.67 lbf, respectively. (Note: it took 3 trials to remove foam. The foam slipped off the gripper during the first two trials. |
| Control 2 - Noncorrugated tissue contact layer | Minimal granulation | 2.66 lbf |
| Example 3 | Good granulation and texture of microcorrugation was visible in the wound | 2.27 lbf |
| Control 3 - Traditional wound packing | Granulation only on one side | Not Determined |

Note:
the units of the force measurements are listed in foot-pounds.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. An article comprising a macroporous wound-packing material coupled to a microcorrugated microporous wound-contact layer comprising a plurality of ridges extending in a longitudinal direction and grooves extending in a longitudinal direction along the microporous layer, wherein a plurality of micropores are distributed along the plurality of ridges and grooves, the plurality having an average pore diameter; wherein the average pore diameter of the micropores is less than 25 µm; wherein the microporous layer comprises a woven fabric or knit fabric having uniform micropore dimensions.

2. The article of claim 1, wherein the microporous layer comprises a plurality of alternating ridges and grooves; wherein the plurality of the ridges have a distance between adjacent ridges; wherein, in a relaxed, dry state, an average distance between adjacent ridges of the plurality of ridges is about 0.4 mm to about 5.0 mm.

3. The article of claim 1, wherein the microporous layer comprises a plurality of alternating ridges and grooves, each groove having a depth; wherein, in a relaxed, dry state, the depth is about 0.2 mm to about 2 mm.

4. The article of claim 1, wherein the macroporous material comprises pores having a pore diameter that is about 200 µm to about 5000 µm.

5. The article of claim 1, wherein the wound-packing material comprises a major surface that faces the microporous layer, wherein at least a portion of the surface comprises a plurality of alternating ridges and grooves.

6. The article of claim 1, further comprising an active agent disposed on and/or in the microporous layer.

7. The article of claim 1, wherein the microporous layer comprises a plurality of alternating ridges and grooves, each groove having a longitudinal dimension; wherein, in a relaxed, dry state, the longitudinal dimension extends at least about 0.5 cm.

8. The article of claim 1, wherein the microporous layer or the wound-packing material comprises a material that is radiodense relative to wound tissue.

9. A kit comprising the article of claim 1, wherein the article is dimensioned for positioning in a wound bed.

10. The kit of claim 9, wherein the article comprises plurality of segments, wherein each segment of the plurality of segments comprises the microcorrugated microporous layer and the macroporous wound-packing material, wherein the plurality of segments comprises a first segment and a second segment coupled to the first segment.

11. The kit of claim 9, wherein the microporous layer comprises a plurality of alternating ridges and grooves; wherein the plurality of the ridges have a distance between adjacent ridges; wherein, in a relaxed, dry state, an average distance between adjacent ridges of the plurality of ridges is about 0.4 mm to about 5.0 mm.

12. The kit of claim 9, wherein the microporous layer comprises a plurality of alternating ridges and grooves, each groove having a depth; wherein, in a relaxed, dry state, the depth is about 0.2 mm to about 2 mm.

13. The article of claim 1, wherein the microporous layer is a non-adherent contact layer.

14. The article of claim 13, wherein the non-adherent contact layer is nylon.

15. An article comprising a macroporous wound-packing material enveloped in a microcorrugated microporous wound-contact layer comprising a plurality of micropores distributed along a plurality of ridges extending in a longitudinal direction along the microporous layer and grooves extending in a longitudinal direction along the microporous layer, the plurality of micropores having an average pore diameter; wherein the average pore diameter of the micropores is less than 25 µm; wherein the microporous layer comprises a woven fabric or knit fabric having uniform micropore dimensions.

16. The article of claim 15, wherein the plurality of ridges extend at least 0.5 cm in the longitudinal direction and the plurality of grooves extend at least 0.5 cm in the longitudinal direction along the microporous layer.

17. An article, comprising:
a plurality of segments, each segment comprising a macroporous wound-packing material enveloped in a microcorrugated microporous wound-contact layer;
wherein the microcorrugated microporous layer comprises a woven fabric or knit fabric having a plurality of pores, the plurality having a uniform pore diameter, wherein the average pore diameter is less than 25 µm,
wherein the microcorrugated microporous layer has a plurality of longitudinally extending ridges and longitudinally extending grooves; and
a tether connecting a first segment to a second segment.

18. A method, comprising:
positioning a first major surface of a microcorrugated microporous layer in contact with a wound surface of a wound bed;
wherein the microporous layer is dimensioned for positioning against the wound bed;
wherein the microporous layer comprises a plurality of ridges and grooves extending in a longitudinal direction along the microporous layer
wherein the microporous layer comprises a woven fabric or knit fabric having uniform micropore dimensions and a plurality of micropores distributed along the plurality of ridges and grooves, the plurality of micropores having an average pore diameter;
wherein an average pore diameter of the micropores is less than 25 µm;
positioning a macroporous wound-packing material proximate a second major surface of the microporous layer;
wherein positioning the macroporous material proximate the microporous layer comprises positioning the microporous layer between the wound surface and the macroporous material;
covering the wound surface, the layer, and macroporous material with a liquid-impermeable drape; and
placing the macroporous material into fluid communication with a source of negative pressure.

19. The method of claim 18, wherein the macroporous material is coupled to and/or substantially surrounded by the microporous layer, wherein positioning the first major surface of the microporous layer proximate the wound surface comprises simultaneously positioning the macroporous material proximate the wound surface, wherein the microporous layer is positioned between the wound surface and the macroporous material.

20. The method of claim 18, wherein the drape further comprises a port, wherein placing the macroporous material into fluid communication with the source of negative pressure comprises connecting the source of negative pressure to the port.

21. The method of claim 18, wherein placing the wound area into fluid communication with the source of negative pressure comprises subjecting the wound area to a negative pressure of about −20 Torr to about −300 Torr.

* * * * *

UNITED STATES PATENT AND TRADEMARK OFFICE
CERTIFICATE OF CORRECTION

PATENT NO. : 10,813,793 B2
APPLICATION NO. : 15/129434
DATED : October 27, 2020
INVENTOR(S) : Simon Fung Page 1 of 1

It is certified that error appears in the above-identified patent and that said Letters Patent is hereby corrected as shown below:

In the Specification

<u>Column 10</u>
Line 54         Delete "Jim," and insert -- µm, --, therefor.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*